United States Patent [19]

Inoue et al.

[11] Patent Number: 5,305,076
[45] Date of Patent: Apr. 19, 1994

[54] QUANTITATIVE ANALYTICAL METHOD AND APPARATUS FOR SPECTROMETRIC ANALYSIS USING WAVE NUMBER DATA POINTS

[75] Inventors: Kaori Inoue, Hirakata; Yutaka Yamagishi, Yasu; Masayuki Adachi, Kyoto, all of Japan

[73] Assignee: Horiba, Ltd., Kyoto, Japan

[21] Appl. No.: 836,786

[22] Filed: Feb. 14, 1992

[30] Foreign Application Priority Data

Feb. 16, 1991 [JP] Japan .................... 3-044166
Feb. 16, 1991 [JP] Japan .................... 3-044167
Feb. 21, 1991 [JP] Japan .................... 3-048864
Feb. 23, 1991 [JP] Japan .................... 3-050853

[51] Int. Cl.$^5$ ............................................. G01B 9/02
[52] U.S. Cl. ........................... 356/346; 356/319; 356/326; 250/339.01
[58] Field of Search ............ 356/346, 319, 326; 250/339, 343

[56] References Cited

U.S. PATENT DOCUMENTS 4,927,269 5/1990 Keens et al. ..................... 356/346

OTHER PUBLICATIONS

L. de Galan, "Analytical Spectrometry", London (1971), pp. 73–84.
P. R. Griffith et al., "Fourier Transform Infrared Spectrometry", New York (1986) Chapter 10, Quantitative Analysis, pp. 338 to 368.
W. Bruegel, "Einfuehrung in the Ultrarotspektroskopie", Darmstadt (1962), pp. 314 to 343.
A. L. Smith, "Applied Infrared Spectroscopy", New York (1979), pp. 219 to 250.

Primary Examiner—Samuel A. Turner
Assistant Examiner—La Charles P. Keesee, II
Attorney, Agent, or Firm—Price, Gess & Ubell

[57] ABSTRACT

A method and apparatus to determine the constituent ingredients in a sample by a spectroscopic procedure is disclosed. A Fourier transformation infrared spectrometer can secure data of a power spectrum of a sample and data of a power spectrum of a reference. A absorption spectrum of the sample from this respective data can be determined. A set of wave number points across the absorption spectrum of the sample that exhibit a predetermined linear characteristic can be selected and the absorption spectrum values corresponding to the set of wave number points can be used to calculate the concentrations of the constituent ingredients. A plurality of sets of wave number points can also be predetermined for a specific sample and limit values can be stored and compared to pick the most desirable set of wave number points for calculating the concentration of the constituent ingredients.

8 Claims, 15 Drawing Sheets

Fig. 8 (A)
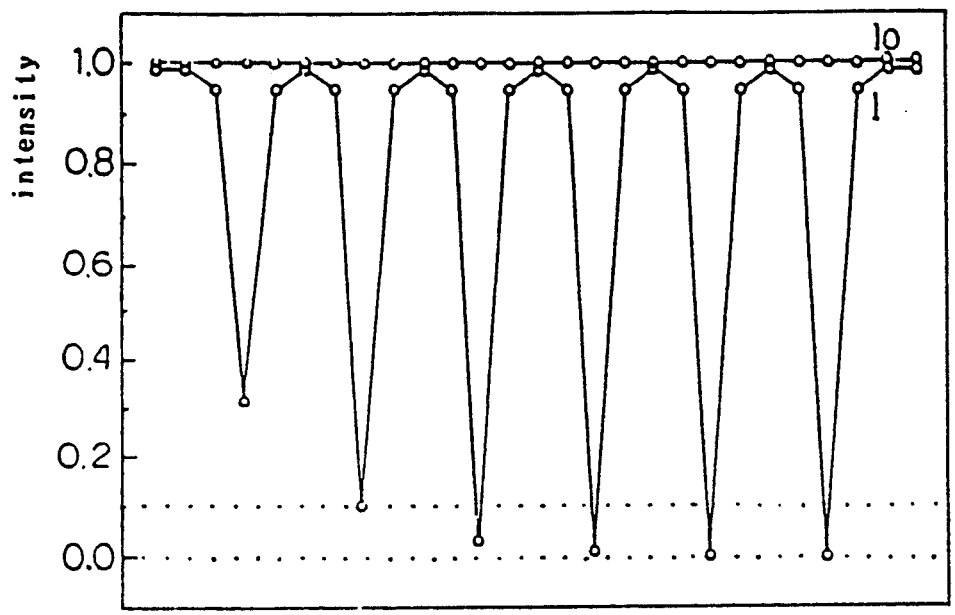
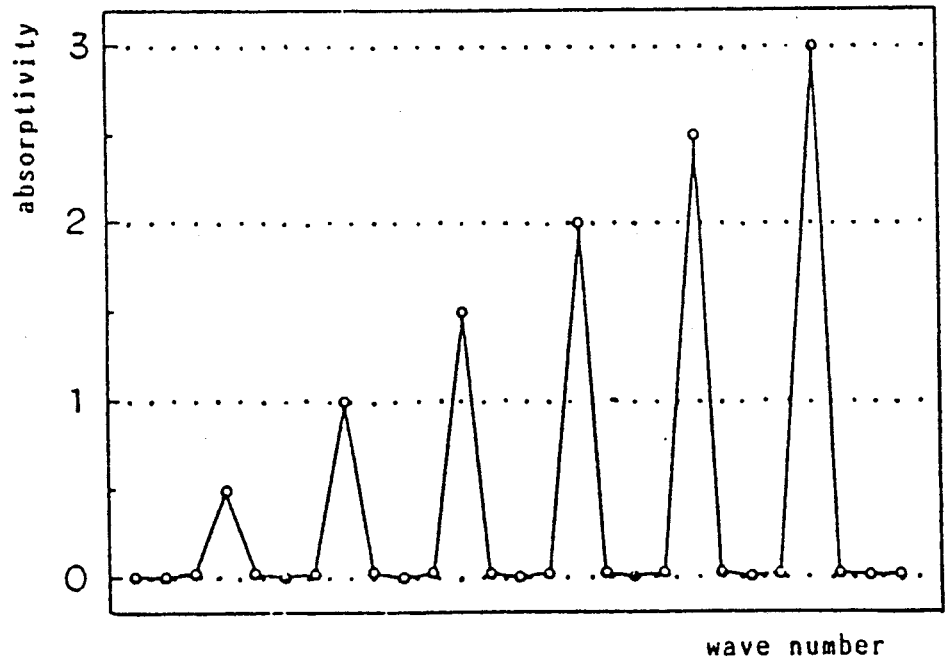
Fig. 8 (B)

(A)

(B)

QUANTITATIVE ANALYTICAL METHOD AND APPARATUS FOR SPECTROMETRIC ANALYSIS USING WAVE NUMBER DATA POINTS

BACKGROUND OF THE INVENTION

1. Field of the Invention

The present invention relates to a quantitative analytical method and apparatus for spectrometric analysis in which a sample is irradiated with light radiation such as infrared light, and a concentration of ingredients contained in the sample are measured on the basis of absorptivities at a plurality of appointed wave number points across an absorption spectrum.

2. Description of Related Art

A Fourier transformation infrared spectrometer (hereinafter referred to as FTIR) 1 having a construction as shown in, for example, FIG. 1, has been used for quantitative analytical results. The FTIR 1 is composed of an analytical portion 2 and a data-treating portion 3 for processing an interferogram which is the output of the analytical portion 2.

The analytical portion 2 is further composed of a light source 4 constructed so as to emit parallel infrared beams, an interference mechanism 8 comprising a beam-splitter 5, a fixed mirror 6, and a movable mirror 7 movable in the X-Y direction, a cell 9 housing a sample to be measured therein and irradiated with the infrared beams from the light source 4 through the interference mechanism 8, and a detector 10 composed of a semiconductor detector and the like.

The data-treating portion 3 comprises a spectrum-operating portion 11 processing an absorption spectrum of data composed of, for example, a computer and a quantitative operating portion 12 capable of calculating concentrations of ingredients contained in the sample to be measured by applying Lambert-Beer's law to the calculated absorption spectrum In addition, the spectrum-operating portion 11 comprises an adding and averaging portion 13 for adding and averaging, for example, the data of the interferogram, a high-speed Fourier transforming portion 14, in which output data from the adding and averaging portion 13 are subjected to a high-speed Fourier transformation, and an operating portion 15 for carrying out a spectral operation to determine the ingredients to be measured on the basis of output data from the high-speed Fourier transforming portion 14.

In an FTIR 1 having the above-described construction, a reference sample and an unknown sample to be measured, are separately housed in the cell 9 in order to measure an interferogram of the reference sample and of the sample to be measured, respectively. These interferograms are subjected to a Fourier transformation to obtain a characteristic power spectra; that is, a spectra of beams which have been transmitted through the cell 9. A ratio of the power spectrum of the sample to be measured to the power spectrum of the reference sample is then determined. A value of this ratio is converted to an absorptivity scale to obtain the absorption spectrum of the sample.

In the quantitative operating portion 12, which is a latter stage of the data-treating portion 3, the concentrations of the ingredients contained in the sample to be measured can be calculated by applying Lambert-Beer's law to the calculated absorption spectrum Problems have occurred in the prior art where concentrations of a sample can vary across a significant range. Also, when the sample contains multiple ingredients which are to be simultaneously analyzed during a continuous measurement cycle, and the amount of concentration of individual ingredients can vary widely, it is difficult to secure accurate readings These problems frequently occur in the analysis of the by-products of combustion from vehicles Accordingly, a demand exists in the prior art to address these problems.

SUMMARY OF THE INVENTION

A first object of the present invention is to provide a method and apparatus capable of quantitatively determining a sample to be measured which is capable of having a wide range of concentration levels without changing the physical or mechanical constitution (or construction) of an analyzer.

In addition, it is a second object of the present invention to provide a quantitative analytical method capable of accurately and continuously analyzing a sample to be measured having concentrations of ingredients which are rapidly changing, such as in a vehicle exhaust.

In order to achieve the first object, wave number points, of which absorptivity within a desirable measurable concentration range has a sufficient linearity, are selected from an absorption spectrum to calculate the concentrations of the ingredients to be measured on the basis of values of absorptivity.

In addition, in order to achieve the second object, a set or plurality of groups of wave number points for use in a calculation of concentrations corresponding to a plurality of concentration ranges of the ingredients to be measured are previously appointed. In an analysis, first one set corresponding to an appointed concentration range of the plurality of groups of wave number points is used to carry out the calculation of concentrations, and then the result of the calculation is compared with a ceiling or limit value. If the preset limit value is exceeded, then the appointed concentration range is changed to a more suitable concentration range to again calculate the concentrations of the respective ingredients by the use of a second group of wave number points corresponding to a more suitable concentration range when it is judged that the appointed concentration range is unsuitable.

The concentration range can be optionally changed by selectively using only the wave number points within an absorptivity range, where a linearity is still observed within the desirable measurable concentration range. Also, an influence by sources of error, e.g., noise, is comparatively small and, thus, a result superior in linearity can be obtained. This operation can be performed by programs within a data-treating device such as a computer, which can select which wave number points are to be used for a calculation of concentrations. Accordingly, it becomes possible to quantitatively determine a sample to be measured having a wide range of concentrations without requiring any changes in the physical or mechanical operation of an analyzer.

The group of wave number points used for a calculation of concentrations of ingredients on the basis of spectral data can be changed, depending upon the specific concentrations of the ingredients contained in the sample to be measured, so that high concentrations can be accurately measured by maintaining a minimum detecting sensitivity as constant, and a continuous analysis can be accurately achieved over a wide range of concentrations. Any changeover of wave number points can be automatically carried out by the computer so that a sample having concentrations of the ingredients which are rapidly changing can be continuously analyzed. In addition, any recalculation need not be carried out on a frequent basis when the concentration change is small. Thus, an advantage occurs in that any loss of measurement time is reduced.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIGS. 8(A) and 8(B) are diagrams showing the relationship between a wave number and intensity of light and the relationship between said wave number and absorptivity;

DESCRIPTION OF THE PREFERRED EMBODIMENTS

Figure 1:
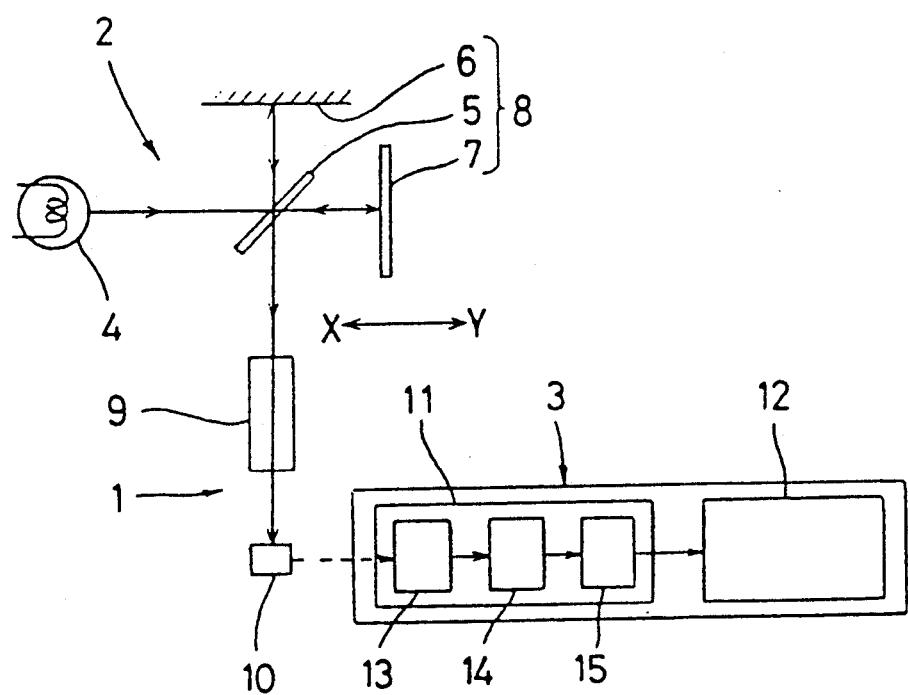
FIG. 1 is a drawing schematically showing one example of an FTIR structure.

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide a method and apparatus for spectrometric analysis.

To provide additional background, one of the present inventors has filed a Japanese Patent Application No. HEI 2-171038, assigned to the present assignee, wherein relative absorptivities, which are the differences between the local peak values and local valley values at a plurality of wave number points in an absorption spectrum, are summed up, and concentrations of the respective ingredients are separately obtained on the basis of the resulting sum. According to this quantitative analytical method, a single ingredient or a plurality of ingredients contained in the sample to be measured can be quantitatively determined by suitably selecting a group of wave number points in the absorption spectrum.

An intensity of light having a certain wave number, which has transmitted through a reference sample and a sample to be measured, respectively, is $I_0$ and $I$, respectively, and an absorptivity $A$ at said certain wave number is represented by $A = \log(I_0/I)$. According to Lambert-Beer's law, the absorptivity $A$ is proportional to a concentration in the sample to be measured. In fact, as can be understood from FIGS. 8(A) and 8(B) showing the relationship between the wave number and the intensity of light in an upper column and the relationship between the wave number and the absorptivity $A$ in a lower column, 90% of the light is absorbed when the absorptivity is 1.0, and 99% of light is absorbed when the absorptivity is 2.0; that is, the above-described relationships do not disclose a boundless linearity. In particular, in a real spectrometer an error (noise) always occurs, and the influence by the error is increased when the denominator in $I_0/I$ approaches zero. In general, if the absorptivity is increased to some extent, the linearity between the absorptivity $A$ and the concentration of the sample to be measured is lost.

When an ingredient to be measured is quantitatively determined on the basis of an absorptivity (or a transmissivity) within a continuous wavelength or wave number range, such as in an NDIR (Non Dispersive Infrared) method, a measurable concentration range is determined by a construction of an analytical portion. In order to change the measurable concentration range, a change in the analyzer construction, such as the regulation of the quantity of light absorbed by changing an optical path length of a cell and a change of an optical filter regulating a range of wavelengths used to one having a different transmission range has been required. Consequently, even though the same ingredient is to be measured, in the case where the concentration is remarkably different, it has been required that at least two analyzers or at least two analytical portions are prepared.

Figure 9:
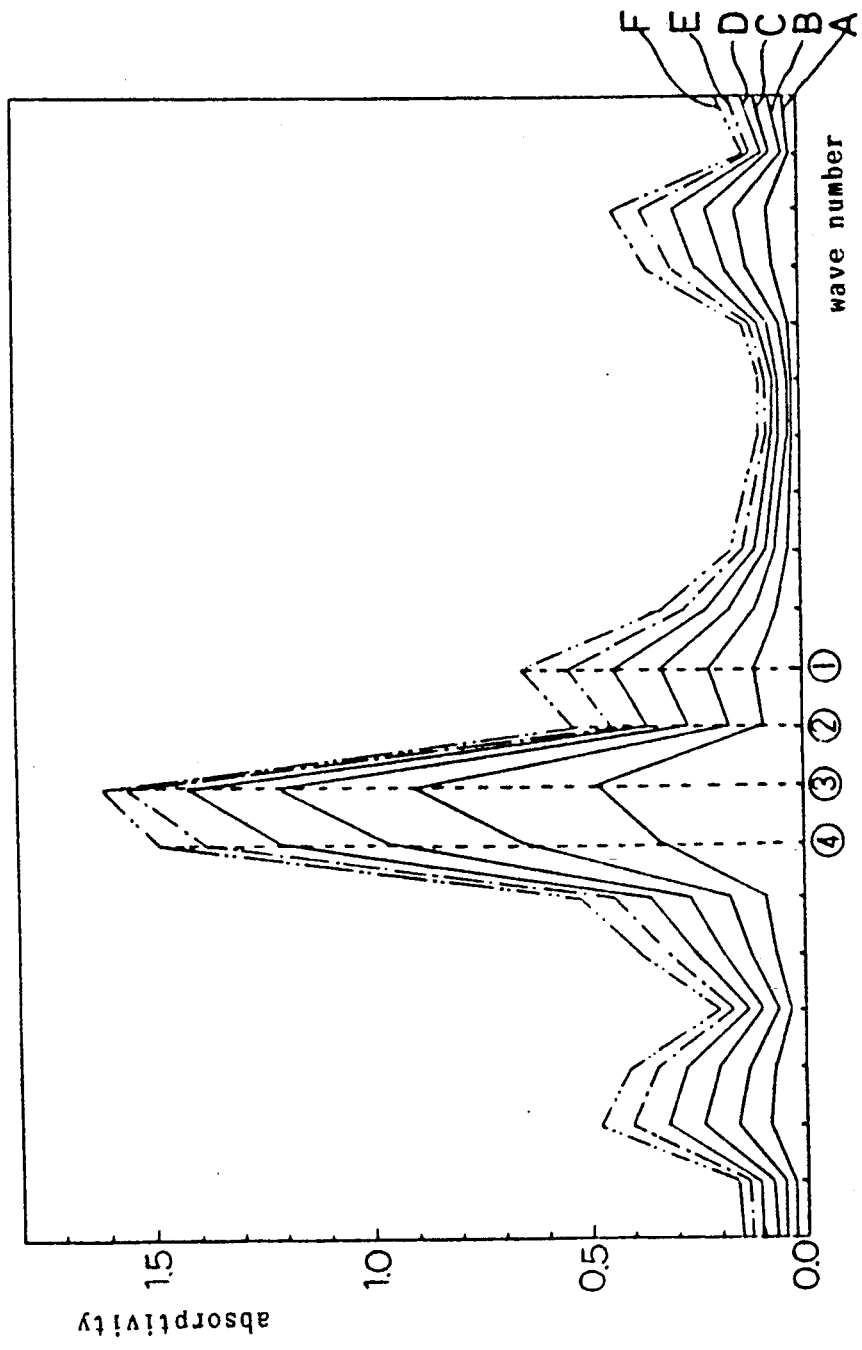
FIG. 9 is a diagram showing illustrative changes of a spectrum curve shape when a concentration of a certain ingredient is changed.
Figure 10:
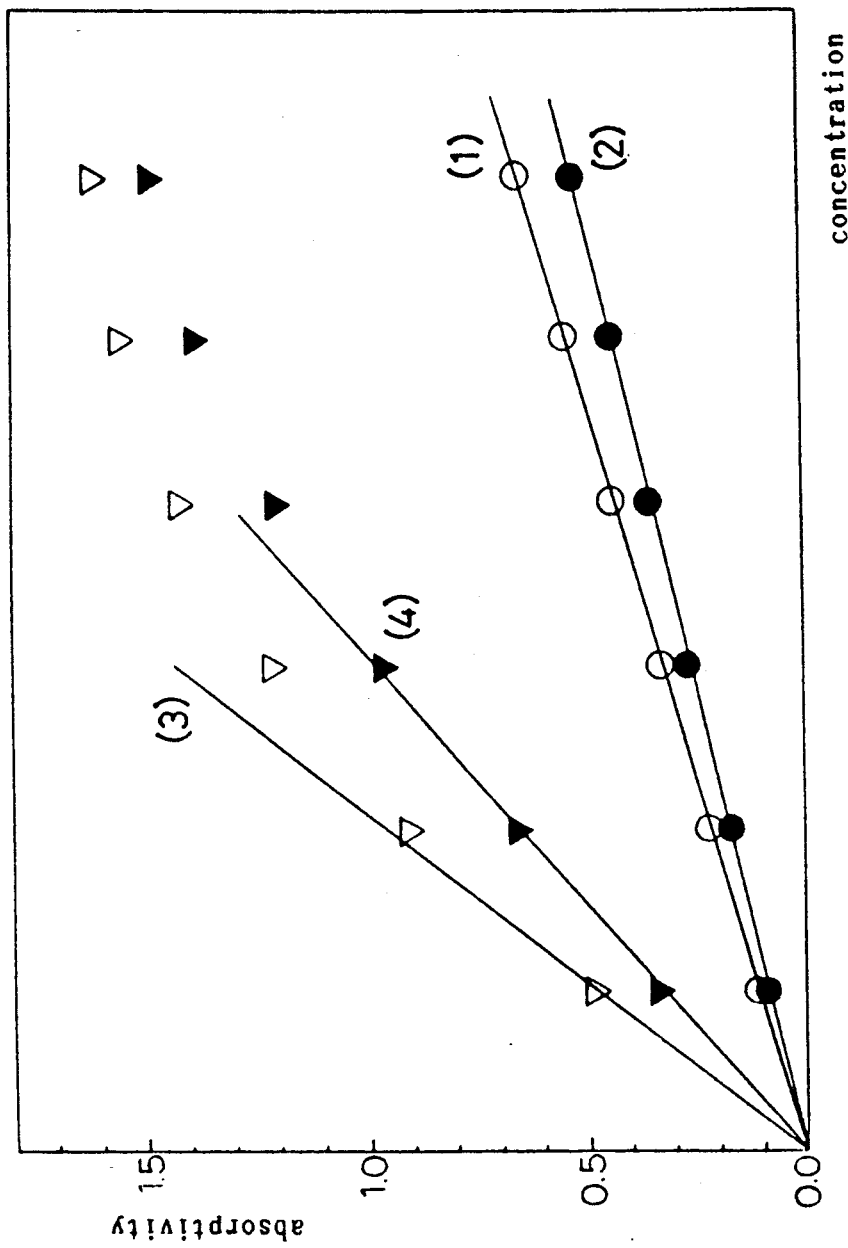
FIG. 10 is a diagram showing the relationship between a concentration of an ingredient and an absorptivity at a certain wave number point in FIG. 9.

From an individual observation of the wave number points in the absorption spectrum obtained by means of the FTIR, the relationship between the concentration of a certain ingredient and its absorptivity at four wave number points ①, ②, ③, ④ can be seen in FIG. 9 for changes of spectra A, B, C, D, E, F in shape corresponding to a change in the concentration of a certain ingredient over six steps. For example, one time, two times, three times, four times, five times, and six times from (a) are shown by four plots (1), (2), (3), and (4) in FIG. 10. As is obvious from these drawings, a skirt portion of the absorption (wave number point ②) and a small peak (wave number point ①) still retain an approximate linearity even though the concentration at which a summit of a large peak of the absorption (wave number point ③ or ④) has already lost its linearity.

Basically, as used herein, the term "linearity" refers to a sufficient proportional relationship between the optical absorption coefficient A at a certain wave number point and a sample concentration C, such as $A \simeq K \times C$, where K is a constant.

The specific selection of wave number points, in a quantitative determination, is based on a sufficient difference between corresponding peak values and valley values to be effective in providing a characteristic absorption of an ingredient. The specific set of wave numbers to constitute a measurement range can vary with the expected level of concentration of one or more ingredients.

However, in cases where the ingredient in the sample to be measured is quantitatively determined by the use of the FTIR, the concentration range, where the concentration can be accurately calculated, of a certain group of wave number points for use in the calculation of concentrations, is comparatively narrow. In short, a high concentration cannot be correctly analyzed by using a group of wave number points for use in the calculation of low concentration, while a low concentration cannot be detected by using a group of wave number points for use in the calculation of high concentration, due to a deterioration of a minimum detecting sensitivity. For example, if the concentration range is 0 to 100 ppm and the noise is zero at 1% of FS (full scale), detection is possible up to about 2 ppm, but in the case where the concentration range is 0 to 1,000 ppm, only the concentration of about 20 ppm or more can be detected, even though the noise is zero at 1% of FS. Because a level of zero noise relative to the full scale is not dependent upon the concentration range so much, an absolute value of the noise is increased for the high concentration range.

Figure 11A:
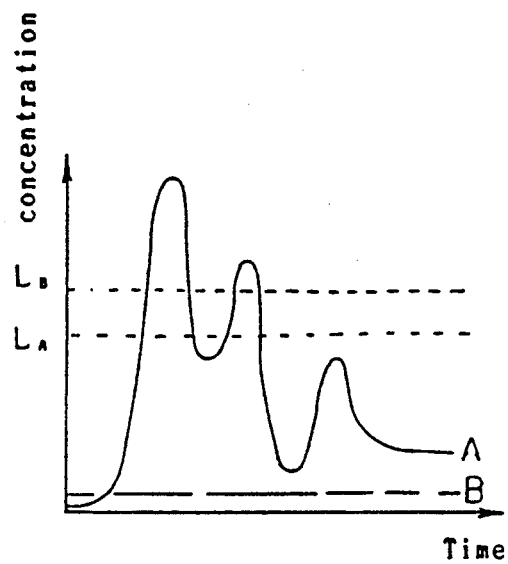
FIG. 11(A) is a wave-shape diagram showing an actual concentration change.
Figure 11B:
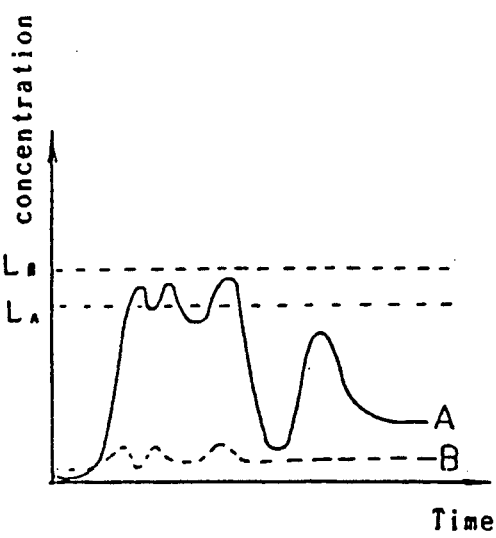
FIG. 11(B) is a diagram showing a change of a calculated concentration value in output.

In addition, in case of a simultaneous multiple-ingredient analysis in which, for example, two ingredients to be measured A, B are simultaneously analyzed, as shown in FIG. 11(A), not only a calculated concentration value of the ingredient to be measured A, but also a calculated concentration value of the other ingredient to be measured B having a low concentration, which does not exceed a measurable limit $L_A$, becomes inaccurate if a concentration of one ingredient to be measured A exceeds a measurable limit $L_A$. This is further graphically shown in FIG. 11(B). Accordingly, a highly accurate analysis has not been able to be satisfactorily achieved in a continuous measurement of a sample to be measured when concentrations of constituent ingredients are rapidly changed, such as in an exhaust gas from automobiles.

A quantitative analytical method by the use of spectrometric analysis according to the present invention is different from the conventional method in that only a predetermined number of wave number points, having an absorptivity within a desirable measurable concentration range of a sufficient linearity, are selected from an absorption spectrum to calculate concentrations of ingredients to be measured on the basis of values of absorptivity.

Figure 2:
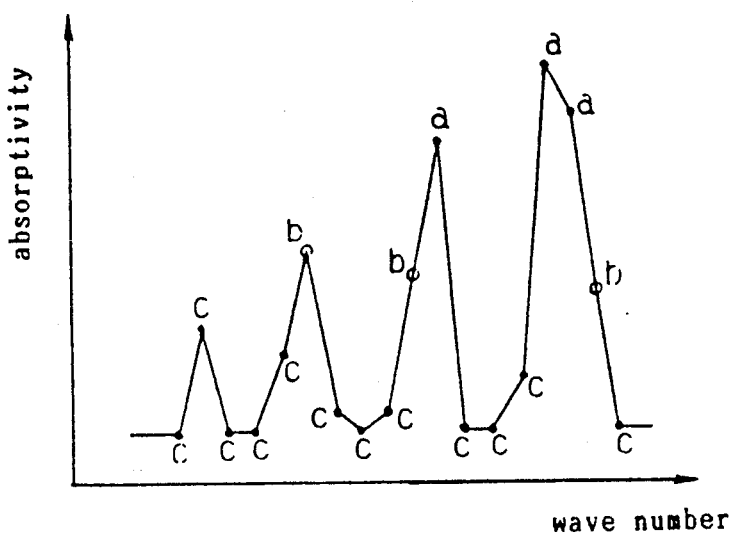
FIG. 2 is a diagram showing one example of an absorption spectrum with groups of wave number points.

Provided that a compound has an absorption spectrum as shown in FIG. 2, marks (a), (b), and (c) designate wave number points, and a plurality of wave number points for use in a calculation of concentrations are suitably selected from all the wave number points (a), (b), and (c) when a comparatively low concentration is analyzed. In addition, a plurality of wave number points for use in a calculation are suitably selected from the wave number points (b) and (c) when a little higher concentration is being analyzed. A plurality of wave number points for use in a calculation are suitably selected from only the wave number points (c) when a still higher concentration is analyzed. Furthermore, it is unnecessary that the wave number points used in the calculation of concentrations be limited by summits of absorption peaks. The skirts of the absorption peaks and portions having no absorption may also be selected to carry out a calculation of concentrations.

Figure 3:
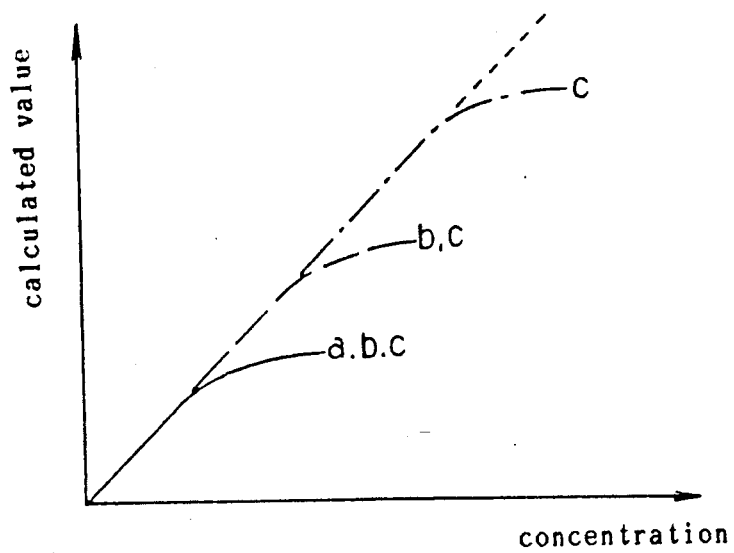
FIG. 3 is a diagram showing the relationship between a concentration of a sample to be measured and a calculated value when a calculation is carried out by a method according to the first object of the invention.

FIG. 3 schematically shows the relationship between an actual concentration of a sample to be measured and a calculated value of concentration of the sample to be measured as calculated by suitably selecting a plurality of wave number points for use in a calculation of concentrations procedure from the wave number points (a), (b), and (c). It can be found from FIG. 3 that a measurable concentration range can be changed by selectively using those wave number points existing within an absorptivity range where the desirable measurable concentration range still has a linearity characteristic and any influence of error is comparatively small. In addition, high concentrations, at which almost all of the wave number points corresponding to the summits of the absorption peaks have lost their linearity, can be calculated.

A quantitative analytical method by the use of a spectrometric analysis according to a second feature of the present invention is greatly different from the conventional method, in that a plurality of kinds of groups of wave number points, for use in a calculation of concentrations (for example, for 0 to 100 ppm, 0 to 1,000 ppm, 0 to 1% and the like), are prepared for a certain ingredient to be measured, depending upon concentration ranges desirably appointed. At the start of a measurement operation, a specified one of these groups of wave number points is used to calculate the concentration. If the calculated value is unsuitable as compared with a predetermined limit or ceiling value, a second group of wave number points, corresponding to a more suitable concentration range, can be used, depending upon the calculated value, to again carry out the calculation. After the second time, as a rule the first group of wave number points is again used to carry out the calculation of concentrations, followed by changing the group of wave number points in the same manner as the above-described operation, depending upon the calculated value, to again carry out the calculation.

Figure 4:
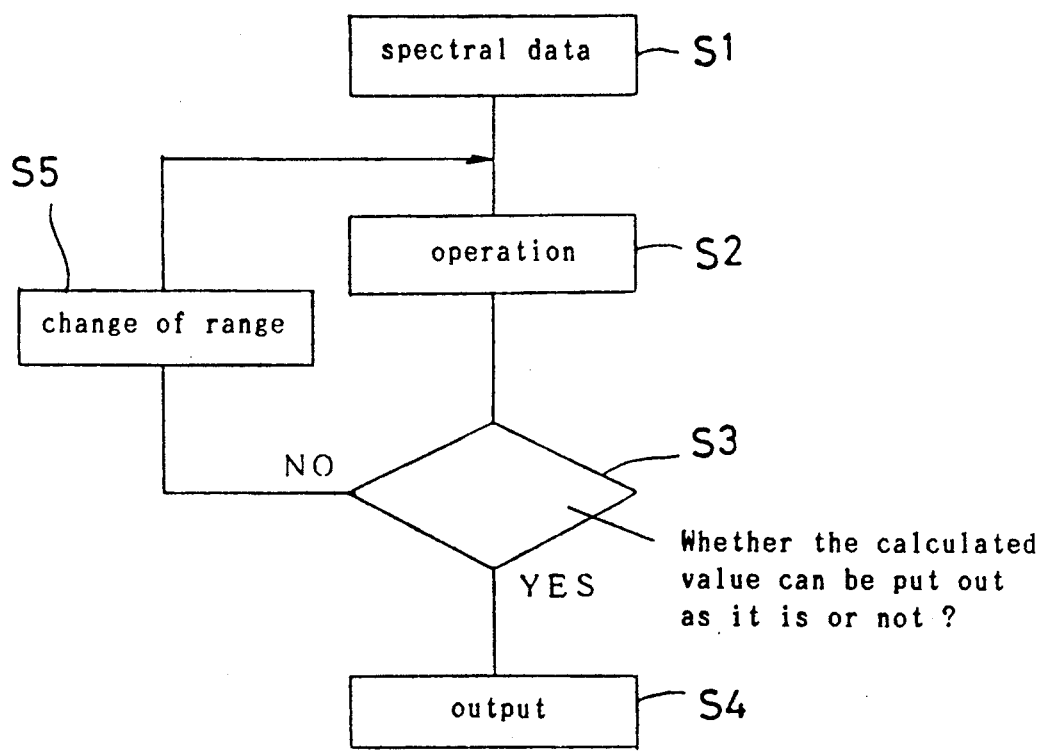
FIG. 4 is a flow chart showing a flow of operations in a method according to the second object of the invention.

Referring to the flow chart of FIG. 4, the group of wave number points for use in a calculation of concentrations corresponding to the setup concentration range is used to carry out an operation (step S2) on the basis of spectral data obtained from an FTIR 1 (step S1). A determination is made by comparing the calculated value with this ceiling value whether or not the calculated value at this time can be used as it is (step S3). In the case where the calculated value can be provided as it is; that is, in the case where a determination is made that the concentration range set up from the calculated value was suitable (YES in step S3), the calculated value is provided as a calculated concentration value (step S4), or else (NO in step S3) the concentration range is changed to a more suitable one (step S5) to carry out the operation from an absorptivity of the corresponding group of wave number points for use in a calculation of concentrations again (step S2).

These procedures of calculation, judgment, and change of range are all automatically carried out within a data-treating portion 3. Thus, only the result of the calculation of concentrations obtained from the most suitable group of wave number points for use in a calculation of concentrations is always provided.

In the case where a calculated value is compared with the ceiling value, it is preferable to also provide a difference between the ceiling value to assist in changing the range from one corresponding to a high concentration to one corresponding to a low concentration, and the ceiling value for changing the range from one corresponding to the low concentration to one corresponding to the high concentration. Thus, a fluctuation in changeover time can be suppressed.

Usually, a ceiling value is set at 80-100% of the desired measuring range of concentration, because the wave number points for use in the calculation of concentration ought to be determined so that the quantitative determination may be accurately achieved until at least 100% of the measuring range of concentration. For example, in the case where the 100-ppm range (hereinafter referred to as L) and the 500-ppm range (hereinafter referred to as H) are to be expected in the sample, 100 ppm is determined as the ceiling value for the changeover of L→H and 90 ppm is determined as the ceiling value in the changeover of H→L. Thereby, the appropriate set of wave number points can be automatically used.

If, for example, the ceiling value in the changeover of L→H and the ceiling value in the changeover H→L are both determined to be 100 ppm, the range could frequently be changed over if a sample having a constant concentration of 100 ppm is continuously measured. The "difference" in ceiling values prevents this problem; that is, if the predetermined ceiling value for the changeover of H→L is determined to be 90 ppm, the concentration will clearly be calculated by merely H.

The above-described method is described for the case where two ingredients A, B are continuously analyzed at the same time. Provided that two ingredients A, B are changed in concentration and the concentration range is automatically changed over to one corresponding to the low concentrations and one corresponding to the high concentrations; i.e., two stages, as shown in FIG. 5, four kinds of groups of wave number points corresponding to combinations of the concentration ranges of the ingredients A, B are defined as shown in Table I.

TABLE I

| | Low Concentration | | High Concentration | |
|---|---|---|---|---|
| Low concentration | l | l | h | l |
| High concentration | l | h | h | h |

Figure 5:
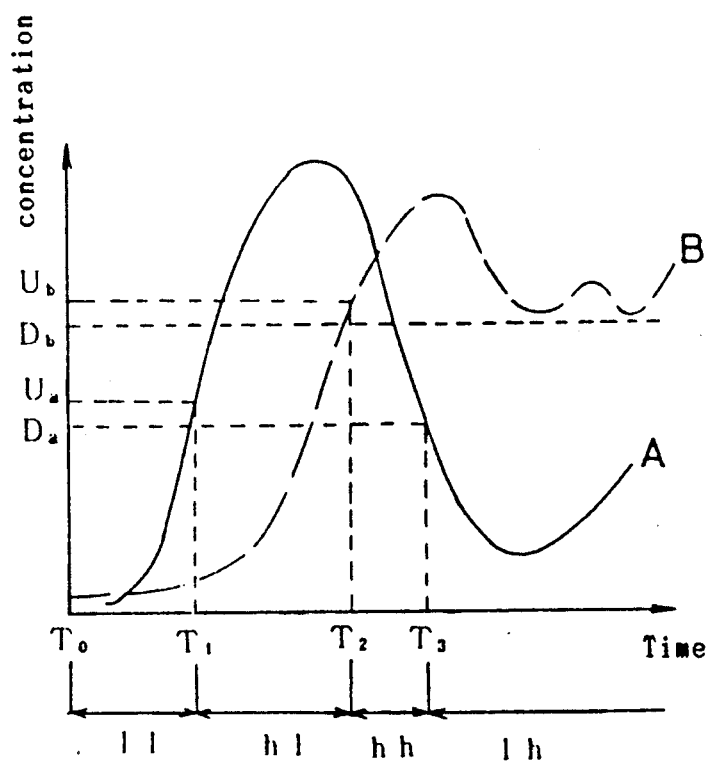
FIG. 5 is a diagram showing one example of an output wave shape.

Provided that the ingredients A, B in a sample are changed in concentration as shown in FIG. 5, the ceiling value from the low concentrations to the high concentrations and the ceiling value from the high concentrations to the low concentrations for the ingredient A being $U_a$, $D_a$ ($U_a > D_a$), respectively, and the ceiling value from the low concentrations to the high concentrations and the ceiling value from the high concentrations to the low concentrations for the ingredient B being $U_b$, $D_b$ ($U_b > D_b$), respectively, the changeover is conducted at times $T_1$, $T_2$, $T_3$. Accordingly, in this example, a concentration value calculated by a group of wave number points ll is provided during a time period from time $T_0$ to time $T_1$, a concentration value calculated by a group of wave number points hl is provided during a time period from the time $T_1$ to the time $T_2$, a concentration value calculated by a group of wave number points hh is provided during a time period from the time $T_2$ to the time $T_3$, and a concentration value calculated by a group of wave number points lh is provided on and after the time $T_3$, respectively.

Figure 12:
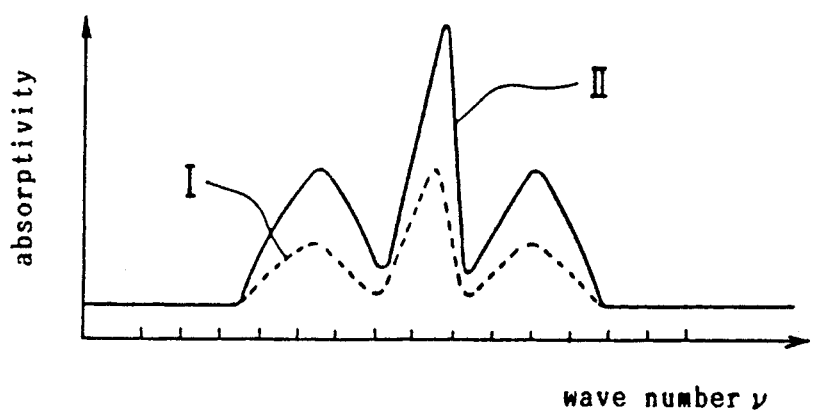
FIG. 12 is a diagram showing a general absorption spectrum for describing the conventional multi-ingredient analytical method.

In the above-described method of analyzing a plurality of ingredients by the use of a spectrometric analysis, a linear algebraic method on the basis of Lambert-Beer's law that the absorptivity is proportional to the concentration of the ingredient to be measured has been generally used. Lambert-Beer's law can be expressed as follows:

$$A(\nu) = C\alpha(\nu) \tag{1}$$

wherein C represents a concentration of an optional absorbent; $\alpha(\nu)$ represents an absorption spectrum of unit concentration at a wave number of $\nu$; and $A(\nu)$ represents an absorption spectrum of an absorbent of unknown concentration at a wave number of $\nu$. This relationship is schematically shown in FIG. 12. Referring to FIG. 12, curve I and curve II show the absorption spectrum $\alpha(\nu)$ of unit concentration and the absorption spectrum of unknown concentration, respectively. In the case where the absorptions of a plurality of ingredients are overlapped, the above-described Equation (1) is expressed by the following merely linear combination (2):

$$A(\nu) = \Sigma_i C_i \alpha_i(\nu) \tag{2}$$

wherein $C_i$ represents concentrations of the respective ingredients, and $\alpha_i$ represents the absorption spectrum of unit concentration for the respective ingredients.

In a spectrometric analysis of a plurality of ingredients by the use of absorption spectra, which has been generally carried out, reference spectra $\alpha_i(\nu)$ for the respective ingredients are previously determined in a calibration stage to estimate the concentrations $C_i$ of the respective ingredients from the absorption spectrum $A(\nu)$ of an unknown mixture to be measured.

Usually, $A(\nu)$ is measured as a value corresponding to the continuous wave number points ranging, for example, from 4,000 cm$^{-1}$ to 400 cm$^{-1}$ in an infrared range, so that Equation (2) is expressed by the following simultaneous equations of the first degree (3):

$$A(\nu_j) = \Sigma_i C_i \alpha_i(\nu_j) \tag{3}$$

Accordingly, the concentrations of a plurality of ingredients can be estimated by carrying out an operation of these simultaneous equations of the first degree by the use of a processional formula.

Figure 13:
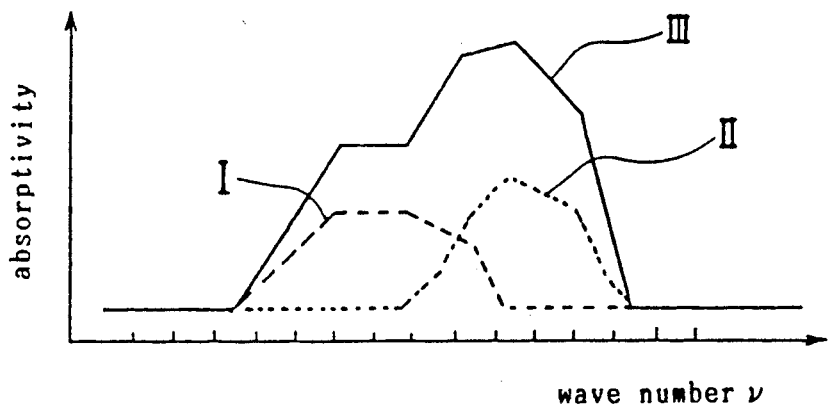
FIG. 13 is a diagram schematically showing spectra of two ingredients piled up.

FIG. 13 schematically shows absorption spectra of two ingredients overlapped. Referring to FIG. 13, curve I and curve II show an absorption spectrum of unit concentration $\alpha_1(v_j)$, $\alpha_2(v_j)$ for an ingredient gas, respectively, and curve III shows a linear combination of those spectra (shown above in Equation (3)).

However, some ingredients, such as carbon monoxide and nitrogen monoxide, contained in the sample to be measured, do not conform to Lambert-Beer's law and, thus, a problem can occur and a great error can be produced in determining the concentrations of these ingredients by the above-described conventional method.

Figure 14:
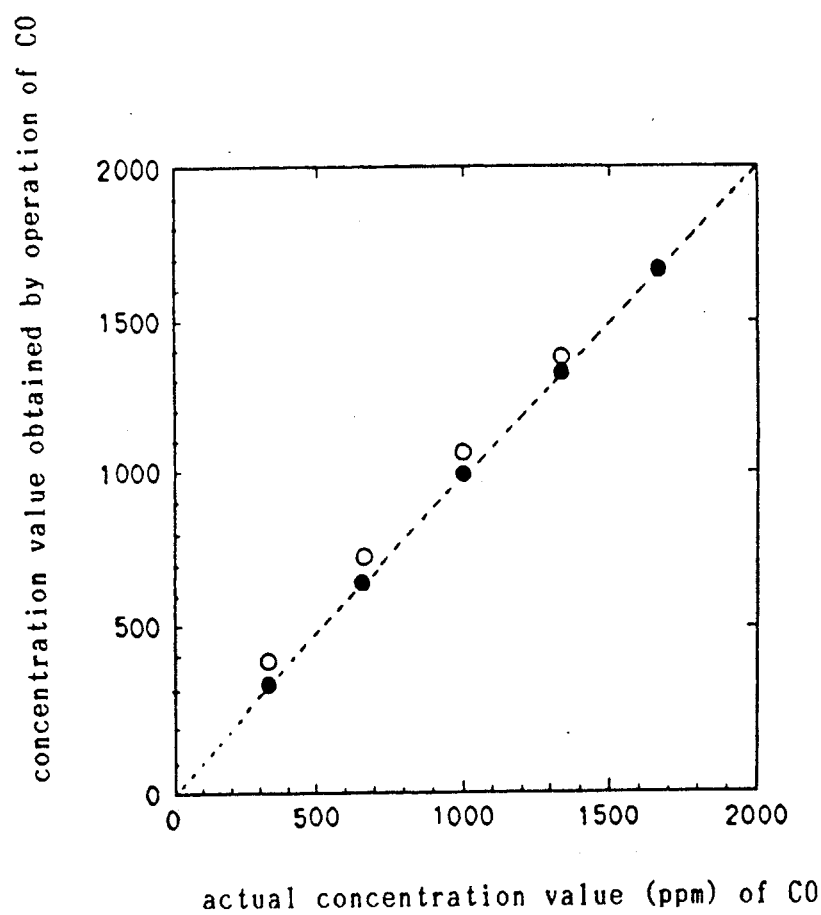
FIG. 14 is a diagram showing a deviation of a concentration value of carbon monoxide obtained from a measurement operation from an actual concentration value.

FIG. 14 shows the difference between an actual concentration value of carbon monoxide and a value measured by the above-described conventional method. An axis of abscissa shows the actual concentration value, and an axis of ordinate shows the operated concentration value. Referring to FIG. 14, marks ○ show a plot of the operated values corresponding to the respective actual concentration values, and marks ● show a plot of correct concentration values to be actually determined as the operated values shown by the marks ○.

Figure 15:
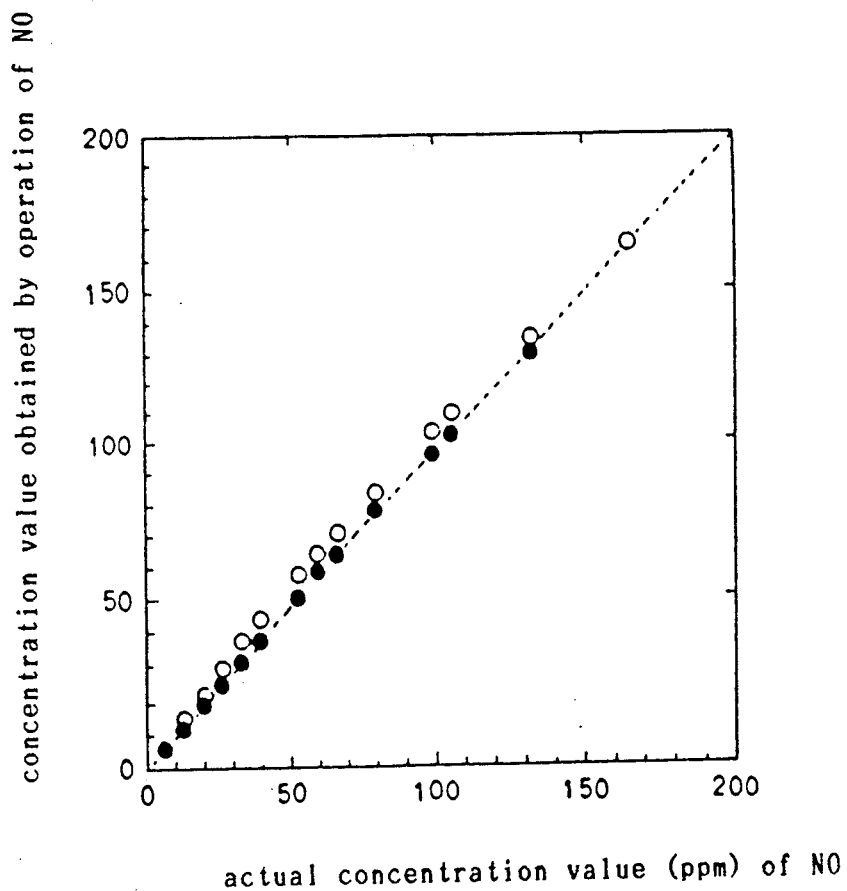
FIG. 15 is a diagram showing a deviation of a concentration value of nitrogen monoxide obtained by a measurement operation from an actual concentration value.

Also, FIG. 15 shows the difference between an actual concentration value of nitrogen monoxide and an operated value in the same manner as shown in FIG. 14.

As obvious from FIGS. 14 and 15, in cases of carbon monoxide and nitrogen monoxide, the concentration values obtained by applying Lambert-Beer's law to the absorption spectrum are different from actually-measured values. These ingredients are of a nonlinear absorption type.

In such cases, it is sufficient that the concentrations of ingredients which do not conform to Lambert-Beer's law are determined by applying an inverse function $A^{-1}(C_x)$ of an approximate formula $A(C)$ to a calculated concentration $C_x$ calculated by applying Lambert-Beer's law to the absorption spectrum. This will be described below.

First, the absorption spectrum (corresponding to $A(v_j)$ in Equation (3)) for the sample to be measured is obtained, and the reference spectra (corresponding to $\alpha_i(v_j)$ in Equation (3)) for the known concentrations of the respective ingredients contained in the sample to be measured are obtained. These values are applied to Equation (3) to solve simultaneous equations of the first degree, thereby calculating the concentrations $C_i$ of the respective ingredients.

Figure 6:
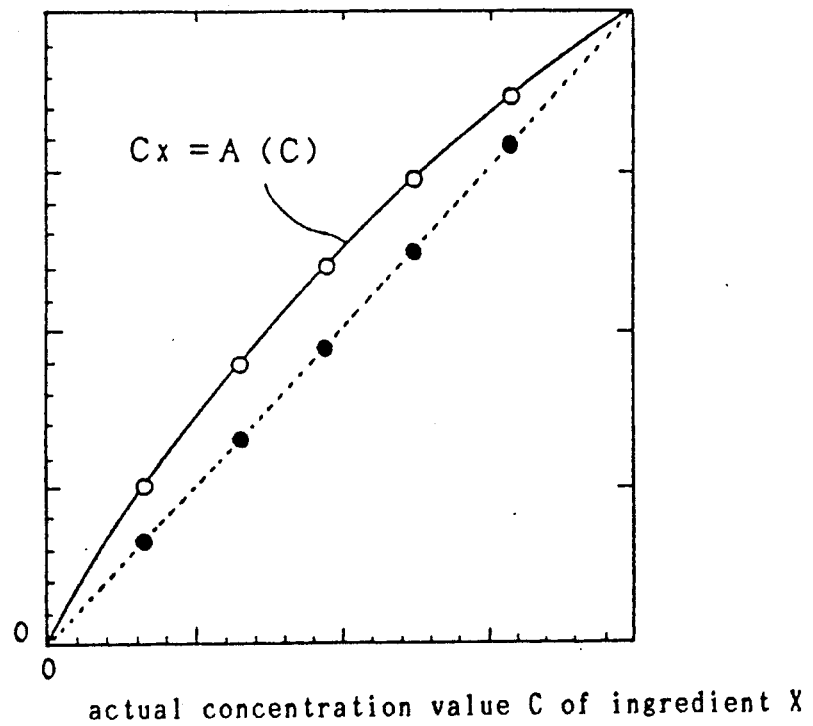
FIG. 6 is a diagram schematically showing a deviation of a concentration value of an ingredient, which does not conform to Lambert-Beer's law, obtained by an operation from an actual concentration value and a curve of an approximate formula representing the concentration value obtained by an operation.

Prior to this, for the ingredients, such as carbon monoxide and nitrogen monoxide, which do not conform to Lambert-Beer's law (generalized here as ingredient X), of the ingredients in the sample to be measured, the following approximate equation of the fourth degree (4) expressing the operated concentration value $C_x$ with the actual concentration value C, as shown by a full line in FIG. 6, is obtained in the same manner as in FIGS. 14 and 15 as a variable is obtained.

$$A(C) = aC^4 + bC^3 + cC^2 + dC \quad (4)$$

wherein a, b, c, and d represent constants, respectively.

FIG. 6 shows the difference between an actual concentration value C of the ingredient X and an operated value $C_x$ calculated from Equation (3). The axis of abscissa shows the actual concentration value C, and an axis of ordinate shows the operated concentration value $C_x$. Referring to FIG. 6, marks ○ show a plot of the operated values corresponding to the respective actual concentration values, and marks ● show a plot of correct concentration values to be actually determined as the operated values shown by the marks ○.

A curve of the approximate equation $A(C)(4)$ shown by a full line in FIG. 6 is obtained so that the marks ○ showing the respective operated concentration values $C_x$ may exist on the curve as far as possible. An example of carbon monoxide and nitrogen monoxide is shown in FIGS. 14 and 15, respectively. As for an approximate equation for the ingredients which do not conform to Lambert-Beer's law, in general, an equation of the fourth degree will approximate the operated values $C_x$ shown by marks ○ but, in case of the ingredients of which operated values $C_x$, shown by marks ○, can be well approximated by other multidegree equations, those multidegree equations may be used as the approximate equation.

In addition, Equation (4) is transformed to obtain its inverse function $A^{-1}(C_x)$. The inverse function $A^{-1}(C_x)$ in this case is a function expressing a value approximate to the actual concentration C with the operated value $C_x$ as a variable.

Thus, of the concentrations $C_i$ of the respective ingredients obtained by operating Equation (3), the concentration value $C_x$ of the ingredient X, which does not conform to Lambert-Beer's law, is compensated by applying the inverse function $A^{-1}(C_x)$ prepared corresponding to the ingredient X thereto. The compensated value is finally adopted as the concentration of the ingredient X in this case.

In the case where the ingredient X is, for example, carbon monoxide and nitrogen monoxide, the operated values $C_x$ calculated by Equation (3) are compensated from the values shown by the marks ○ in FIGS. 14 and 15 to values almost approximate to the values shown by the marks ● shown in FIGS. 14 and 15.

As described above, for the concentrations of the ingredients which do not conform to Lambert-Beer's law, of a plurality of ingredients contained in the sample, the calculated concentrations $C_x$ corresponding to the actually-measured concentrations C of the ingredients which do not conform to Lambert-Beer's law, are previously determined by a multidegree approximate equation $A(C)$, with the actually-measured concentration C as a variable, and a value obtained by applying the calculated concentration $C_x$ to the inverse function $A^{-1}(C_x)$ of the approximate equation $A(C)$ is adopted as the compensated calculated concentration $C_x$.

However, according to Lambert-Beer's law, the absorptivity is proportional to the concentration of the ingredient to be measured, and it is also expressed by the following Equation (5):

$$A = \epsilon \cdot C \cdot L \quad (5)$$

wherein A represents an absorptivity of the sample to be measured, $\epsilon$ represents an absorption coefficient of the sample, C represents a concentration, and L represents an optical path length of the sample.

The concentration of the ingredient is calculated by the use of Equation (5) in the following manner: an absorption spectrum (hereinafter referred to as a reference spectrum) $A_r$ is previously obtained for a reference sample in which the concentration $C_r$ has been known, the same as the sample to be measured. From Equation (5), the following Equation (6) holds good between the reference spectrum $A_r$ and the concentration $C_r$ in this case:

$$A_r = \epsilon \cdot C_r L \quad (6)$$

Subsequently, an absorption spectrum $A_s$ of the sample to be measured, of which concentration $C_s$ has been unknown, is obtained. Also in this case, from Equation (6), the following Equation (7) holds good between the unknown spectrum $A_s$ and the concentration $C_s$:

$$A_s = \epsilon \cdot C_s \cdot L \tag{7}$$

Thus, the following Equation (8) is obtained from Equations (6) and (7):

$$C_s = (A_s/A_r) \cdot C_r \tag{8}$$

In a quantitative operating portion 12 of a data-treating portion 3, the concentration $C_s$ of the ingredient in the sample to be measured is calculated by applying the reference spectrum $A_r$, the unknown spectrum $A_s$, and the known concentration $C_r$ to Equation (8).

In addition, in general, the reference spectra $A_r$ obtained for the respective ingredients and the known concentrations $C_r$ corresponding to the reference spectra $A_r$ are previously memorized as data. In the actual measurement, only the absorption spectrum $A_s$ of the sample having the unknown concentration $C_s$ is obtained, and thus, the reference spectrum $A_r$ of the known sample as the reference datum and the known concentration $C_r$ are applied to Equation (4) to calculate the unknown concentration $C_s$.

Figure 16:
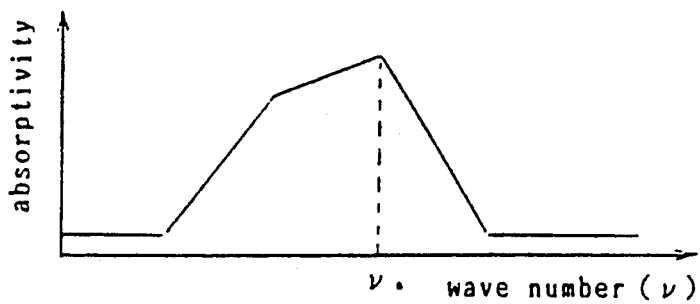
FIGS. 16(A) and 16(B) are diagrams showing a difference in the absorption spectrum of a peak shape resulting from a difference between machines.
Figure 16:
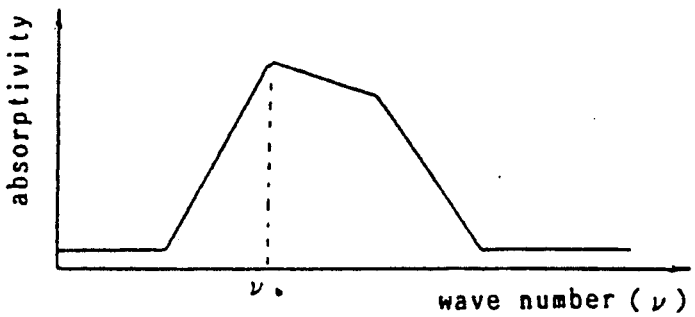

In the case where the FTIRs 1 of the same type are mass produced, a difference frequently occurs among the FTIRs 1 in peak shape of the absorption spectrum obtained for the same sample, due to a difference of machines resulting from slight differences among individual machines in assembly and other conditions, as shown in FIGS. 16(A) and (B). Thus, a problem has occurred in that the concentrations calculated by the individual FTIRs 1 can fluctuate. For example, a peak exists at a wave number point $v_a$ in an absorption spectrum obtained for an optional sample by means of a certain FTIR 1, as shown in FIG. 16(A), while a peak exists at another wave number point $v_b$ in an absorption spectrum obtained for the same sample by means of another FTIR 1, as shown in FIG. 16(B). The differences in spectral shape are due to differences among the individual machines.

Figure 7:
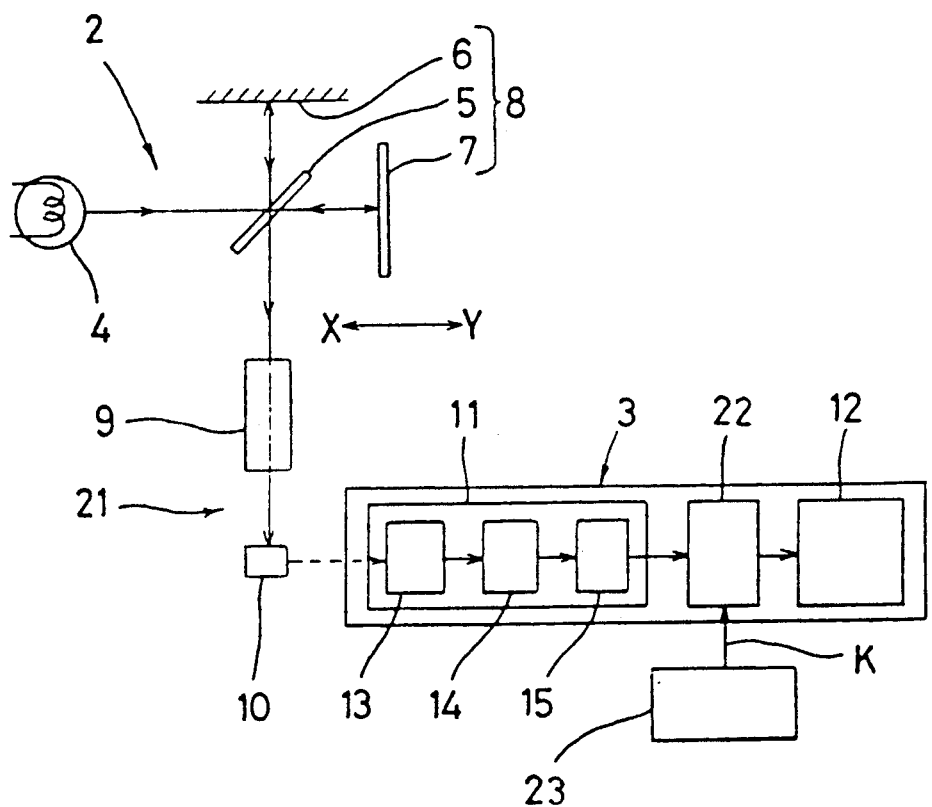
FIG. 7 is a drawing roughly showing an example of another construction of an FTIR structure.

Usually, the wave number points, where the reference spectrum $A_r$ and the unknown spectrum $A_s$ become the peak values, are selected as the wave number points of the reference spectrum $A_r$ and the unknown spectrum $A_s$ to be applied to Equation (8), in order to obtain a high accuracy of measurement, so that if a difference occurs among the individual apparatus at a peak shape of the spectrum in the above-described manner, the value of concentration calculated from Equation (8) also becomes different among the individual apparatus. In such a case, the data-treating portion 3 of an FTIR 21 is adapted to provide a spectrum-compensating portion 22 between a spectrum-operating portion 11 and the quantitative operating portion 12, and to provide a compensation factor K in the spectrum-compensating portion 22 from a factor-setting portion 23, so that the absorption spectrum may be multiplied with the compensation factor K to compensate the absorption spectrum in the spectrum-compensating portion 22, as shown in FIG. 7.

In an analyzing portion 2 of the FTIR 21, an interferogram of the sample, housed in a cell 9, is measured. In the spectrum-operating portion 11, which is the first stage of the data-treating portion 3, the interferogram is subjected to a Fourier transformation to obtain a power spectrum. Then a ratio of the obtained power spectrum to a power spectrum of a reference sample is obtained, followed by transforming the obtained ratio to an absorption scale to calculate the absorption spectrum $A_s$ of the sample to be measured.

The calculated absorption spectrum $A_s$ is multiplied by the compensation factor K by means of the spectrum-compensating portion 22 in the following stage to compensate the absorption spectrum from $A_s$ to $k \cdot A_s$.

The compensated absorption spectrum $k \cdot A_s$ is applied to Equation (8) in the quantitative operating portion 12, which is a latter stage of the data-treating portion 3, to obtain the following Equation (9), thereby calculating the concentration $C_s$ of the ingredient in the sample to be measured.

$$C_s = (K \cdot A_s/A_r) \cdot C_r \tag{9}$$

The compensation factor K is determined in the following manner. An optional sample, of which the concentration has been known, is subjected to a spectrometric analysis by means of the FTIR 21 to calculate the concentration $C_s$ of the ingredient in the optional sample. In the case where the calculated concentration $C_s$ of the ingredient does not coincide with the known concentration, the factor-setting portion 23 is operated so that the calculated concentration $C_s$ of the ingredient may coincide with the known concentration to change the compensation factor K. Such compensation is carried out for every FTIR 21 by using the same sample to eliminate the fluctuation of the measured values due to differences among the FTIRs 21.

In addition, differences are produced in peak shapes of the absorption spectra due to mechanical differences among the individual FTIRs 21, as shown in FIGS. 16(A) and (B), so that even though the absorption spectrum $A_s$ calculated in the spectrum-operating portion 11 is multiplied by the compensation factor K in the above-described manner, the shape of the absorption spectrum appearing, as shown, for example, in FIG. 16(B), cannot be compensated to the shape as shown in FIG. 16(A). However, the unknown spectrum $A_s$ and the reference spectrum $A_r$, which are used for the operation in the quantitative operating portion 12, are values at the appointed wave number point, so it is sufficient that at least the values at the appointed wave number points are multiplied by the compensation factor K to be compensated, thereby compensating the finally-calculated concentration $C_s$ of the ingredient to a correct value.

As described above, in the case where the calculated quantity of the ingredient in the sample to be measured is different from the value to be properly calculated, the compensation factor is variably set so that the calculated quantity of the ingredient may become the correct value, whereby any fluctuation of the measured values due to mechanical differences among the FTIRs can be eliminated.

In addition, the method according to the present invention can be applied not only to an infrared spectrometric analysis, such as an FTIR, but also to spectrometers using ultraviolet rays and visible rays as a light source. It is applied not only to the method disclosed in the above-described Japanese Patent Application No. Hei 2-170138, but may also be applied to other methods.

Those skilled in the art will appreciate that various adaptations and modifications of the just-described preferred embodiment can be configured without departing from the scope and spirit of the invention. As can be appreciated, computer software can be appropriately used to implement calculations, and operator input can be used to select or modify the ceiling limits and predetermined sets of wave number points, depending upon the specific samples to be measured. Therefore, it is to be understood that, within the scope of the appended claims, the invention may be practiced other than as specifically described herein.

What is claimed is:

1. A method of determining the constituent ingredients in a sample by spectroscopy comprising the steps of:
   securing data of a power spectrum of a sample;
   securing data of a power spectrum of a reference;
   deriving an absorption spectrum of the sample from the respective data of the power spectrum of the sample and the reference;
   selecting a set of wave number points across the absorption spectrum of the sample that exhibit a predetermined linearity characteristic between peak and valley values of the absorption spectrum, and
   utilizing the absorption spectrum values corresponding to the set of wave number points to calculate the concentrations of the constituent ingredients.

2. The method of claim 1 further including the step of selecting a plurality of sets of wave number points, each corresponding to a particular range of concentration values and utilizing one of the plurality of sets of wave number points to calculate the concentration of the constituent ingredients.

3. The method of claim 2 further including the step of providing predetermined limit values and comparing the calculated value of the concentration of the constituent ingredients with the limit values and, if the calculated values are beyond the limit values, the step of selecting another of the plurality of sets of wave number points to recalculate the concentration of the constituent ingredients, whereby the procedure is repeated until a calculated value falls within the limit values.

4. In a quantitative analytical method of processing data obtained by use of a spectrometric analysis wherein a sample is irradiated and concentrations of ingredients contained in the sample are determined on the basis of absorption spectrum values, the improvement comprising:
   determining a set of wave number points, in which absorptivity within a predetermined measurable concentration range exhibits a linearity characteristic, and
   using the absorption spectrum values corresponding to the set of wave number points to calculate the concentration of the constituent ingredients.

5. A method of determining the constituent ingredients in a sample by spectroscopy comprising the steps of:
   (a) securing data of a power spectrum of a sample;
   (b) deriving an absorption spectrum of the sample from the respective data of the power spectrum of the sample;
   (c) providing a plurality of sets of wave number points, each corresponding to a particular range of concentration values;
   (d) providing a predetermined limit value of concentration of constituent ingredients;
   (e) selecting one of the sets of wave number points and using the absorption spectrum values corresponding to the selected set of wave number points, to calculate the concentration ingredients;
   (f) comparing the calculated concentration with the limit value and, if the calculated concentration is within the limit value, then providing the calculation concentration as the output, and
   (g) if the calculated concentration is beyond the limit value, then repeating steps (e) and (f) with a different set of wave number points.

6. The method of claim 5, wherein the provided sets of wave number points exhibit a linearity characteristic between an optical absorption coefficient and a sample concentration value.

7. The method of claim 5, further including the step of modifying the output by a predetermined constant value for ingredients that do not conform to the Lambert-Beer relationship.

8. An apparatus for determining the constituent ingredients in a sample comprising:
   a source of light;
   a cell for housing a sample;
   means for irradiating the cell with the source of light to create an interference pattern;
   means for detecting the interference pattern to provide a power spectrum of the sample;
   means for providing an absorption spectrum of the sample from the power spectrum;
   means for selecting a set of wave number points across the absorption spectrum of the sample that exhibit a predetermined linearity characteristic between peak and valley values of the absorption spectrum, and
   means for utilizing absorption spectrum values corresponding to the selected set of wave number points to calculate the concentrations of the constituent ingredients.

* * * * *